(12) United States Patent
Suydam

(10) Patent No.: US 12,023,148 B2
(45) Date of Patent: Jul. 2, 2024

(54) PHYSICAL MOVEMENT TRACKING

(71) Applicant: Zwift, Inc., Long Beach, CA (US)

(72) Inventor: Stephen M. Suydam, Chicago, IL (US)

(73) Assignee: Zwift, Inc., Long Beach, CA (US)

( * ) Notice: Subject to any disclaimer, the term of this patent is extended or adjusted under 35 U.S.C. 154(b) by 1077 days.

(21) Appl. No.: 16/794,737

(22) Filed: Feb. 19, 2020

(65) Prior Publication Data

US 2020/0260995 A1   Aug. 20, 2020

Related U.S. Application Data

(60) Provisional application No. 62/807,539, filed on Feb. 19, 2019.

(51) Int. Cl.
*A61B 5/00* (2006.01)
*A61B 5/11* (2006.01)
(Continued)

(52) U.S. Cl.
CPC ............ *A61B 5/112* (2013.01); *A61B 5/1126* (2013.01); *A63B 22/02* (2013.01); *A63B 24/0062* (2013.01); *A63B 2024/0065* (2013.01)

(58) Field of Classification Search
CPC ....... A61B 5/112; A61B 5/1126; A63B 22/02; A63B 24/0062; A63B 2024/0065
See application file for complete search history.

(56) References Cited

U.S. PATENT DOCUMENTS 2,290,387 A * 7/1942 Russell ................. A61B 5/11
600/595

3,642,279 A * 2/1972 Cutter ................. A63B 22/02
482/54

(Continued)

FOREIGN PATENT DOCUMENTS

| CN | 104722018 A | * | 6/2015 |
| CN | 107029409 A | * | 8/2017 |

(Continued)

OTHER PUBLICATIONS

Støren, Oyvind & Helgerud, Jan & Hoff, Jan. (2011). Running Stride Peak Forces Inversely Determine Running Economy in Elite Runners. Journal of strength and conditioning research / National Strength & Conditioning Association. 25. 117-23.

*Primary Examiner* — Steven J Hylinski
(74) *Attorney, Agent, or Firm* — SoCal IP Law Group LLP; Jonathan Pearce

(57) ABSTRACT

In a system and method for monitoring movement, a movement monitoring device is configured to engage with a rotating belt of a treadmill. The movement monitoring device includes a rotational tracking device to measure rotational motion of the belt and send the rotational motion measurement to a computing device, and a vertical tracking device to measure vertical motion of the belt and to send a vertical motion measurement to the computing device. The system further includes a computing device for receiving the rotational motion measurement and the vertical motion measurement and to generate a Symmetry Index for the user on the rotating belt of the treadmill, the Symmetry Index being a comparison of more than one measure of symmetry for a first leg and a second leg of the user derived from the rotational motion measurement and the vertical motion measurement.

22 Claims, 5 Drawing Sheets

(51) Int. Cl.
*A63B 22/02* (2006.01)
*A63B 24/00* (2006.01)

(56) References Cited

U.S. PATENT DOCUMENTS

| | | | | |
|---|---|---|---|---|
| 5,209,710 A | * | 5/1993 | Shimizu | A63B 22/02 482/54 |
| 5,312,310 A | * | 5/1994 | Shimizu | A63B 22/02 482/54 |
| 7,648,441 B2 | * | 1/2010 | Silk | A61B 5/1038 600/587 |
| 7,922,619 B2 | * | 4/2011 | Ono | A63B 22/0235 482/901 |
| 8,460,001 B1 | * | 6/2013 | Chuang | A63B 24/0062 434/247 |
| 8,480,541 B1 | * | 7/2013 | Brunts | A63B 22/025 482/7 |
| 8,784,274 B1 | * | 7/2014 | Chuang | G16Z 99/00 482/3 |
| 9,526,451 B1 | * | 12/2016 | Berme | A63B 71/0622 |
| 9,916,011 B1 | * | 3/2018 | Berme | G06F 3/011 |
| 10,265,575 B2 | * | 4/2019 | Chou | A61B 5/112 |
| 10,390,736 B1 | * | 8/2019 | Berme | G09G 5/14 |
| 10,881,905 B2 | * | 1/2021 | Flaction | A61B 5/1038 |
| 11,000,733 B2 | * | 5/2021 | Chou | A63B 24/0087 |
| 2006/0276306 A1 | * | 12/2006 | Pan | A63B 22/02 482/54 |
| 2007/0129769 A1 | * | 6/2007 | Bourget | A61B 5/4839 607/45 |
| 2008/0182727 A1 | * | 7/2008 | Uang | A63B 22/0242 482/54 |
| 2009/0023556 A1 | * | 1/2009 | Daly | A63B 24/0062 482/9 |
| 2009/0124938 A1 | * | 5/2009 | Brunner | A61B 5/1038 600/595 |
| 2009/0137366 A1 | * | 5/2009 | Hirata | A61B 5/02438 482/8 |
| 2009/0240171 A1 | * | 9/2009 | Morris Bamberg | A61B 5/1038 600/595 |
| 2010/0035727 A1 | * | 2/2010 | Brunner | A61B 5/1038 482/8 |
| 2011/0208444 A1 | * | 8/2011 | Solinsky | A61B 5/1114 702/41 |
| 2013/0190658 A1 | * | 7/2013 | Flaction | G01P 15/18 600/595 |
| 2016/0114213 A1 | * | 4/2016 | Lee | A61B 5/6802 434/255 |
| 2016/0144226 A1 | * | 5/2016 | Artemiadis | A63B 22/0228 482/54 |
| 2016/0166879 A1 | * | 6/2016 | Dilli | A63B 22/02 482/8 |
| 2017/0165523 A1 | * | 6/2017 | Chou | A63B 24/0087 |

FOREIGN PATENT DOCUMENTS

| | | | | |
|---|---|---|---|---|
| CN | 109079763 A | * | 12/2018 | B25J 9/0006 |
| DE | 202010004213 U | * | 7/2011 | A61B 5/1038 |
| DE | 202010004213 U1 | * | 7/2011 | A61B 5/1038 |
| DE | 102010051083 A1 | * | 8/2011 | A61H 1/0262 |
| JP | 2001299842 A | * | 10/2001 | A61B 5/1038 |
| KR | 20170020876 A | * | 6/2015 | |
| KR | 20170020876 A | * | 2/2017 | |
| WO | WO-2007112092 A2 | * | 10/2007 | A61B 5/0022 |
| WO | WO-2007131542 A1 | * | 11/2007 | A61B 5/1038 |
| WO | WO-2009118399 A2 | * | 10/2009 | A61B 5/0002 |
| WO | WO-2010096691 A2 | * | 8/2010 | A43B 3/0005 |
| WO | WO-2010150260 A1 | * | 12/2010 | A61B 5/1117 |
| WO | WO-2016065077 A1 | * | 4/2016 | A63B 21/0053 |
| WO | WO-2020035106 A1 | * | 2/2020 | A63B 21/1609 |

* cited by examiner

PHYSICAL MOVEMENT TRACKING

RELATED APPLICATION INFORMATION

This patent claims priority from provisional patent application 62/807,539, filed Feb. 19, 2019, entitled PHYSICAL MOVEMENT TRACKING, the entire content of each of which is incorporated herein by reference.

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the Patent and Trademark Office patent files or records, but otherwise reserves all copyright and trade dress rights whatsoever.

BACKGROUND

Field

This disclosure relates to physical movement tracking, and more particularly to tracking of a user's physical movement on exercise equipment for purposes of preventing injury.

Description of the Related Art

Studies, such as "Running Stride Peak Forces Inversely Determine Running Economy In Elite Runners" by Øyvind Støren, Jan Helgerud, and Jan Hoff, published in Journal of Strength and Conditioning Research Volume 25, Number 1, on January 2011 (the entire content of which is incorporated herein by reference), have demonstrated that differences in running techniques, such as variations in cadence, push off force, landing force, contact time, and flight time, can impact the performance of the runner. Further, asymmetry in a runner's technique can be an indicator and/or a predictor of injuries. Specifically, irregularities in any of these variables or a combination of these variables, if detected while running or early in an ongoing running workout can warn an athlete of an impending or possible injury before it occurs.

However, without accurate statistical information about their technique including these variables, runners may miss opportunities for improving their performance, or worse, miss signs of impending or existing injury. A user-friendly approach for monitoring and/or tracking aspects of a runner's stride would be desirable to help runners improve technique and prevent or detect injuries at an early stage. Though focused on running exercises, similar variables and techniques could be applied to other forms of exercise such as cycling or rowing.

DETAILED DESCRIPTION

Methods and systems disclosed herein accurately determine and track aspects of a runner's (or walker's) stride and technique. This statistical information can then be used to determine potential changes or improvements for the runner's technique. Further, the statistical information can be used to determine whether the runner is at risk of injury due to technique. The statistical information may also indicate that the runner is suffering from an injury that was previously unnoticed. This information may be compiled over time for a very accurate comparison, or may be taken from moment-to-moment as exercise is ongoing, or some combination of both to generate the most accurate results for an exercising individual.

For example, the statistical information can indicate that there is an asymmetrical aspect to the runner's stride that the runner has not noticed. As indicated above asymmetry can indicate an existing injury or may result in a new injury to the runner. The asymmetry may be the result of an existing injury, such that the runner is unconsciously favoring one side over the other. The statistical information can indicate to the runner that the asymmetry is occurring so that the runner can take steps to avoid or recover from injury.

Figure 1:
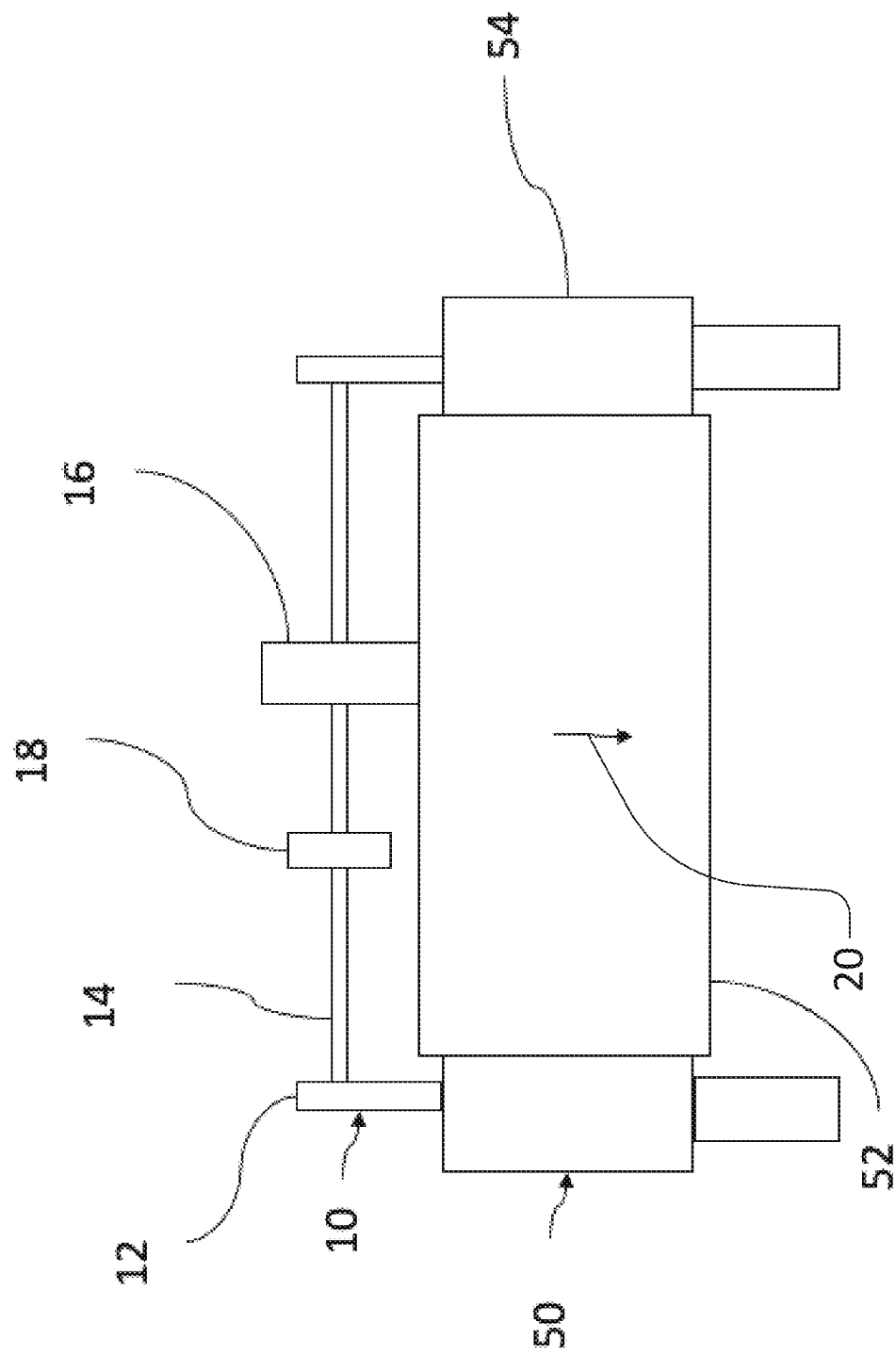
FIG. 1 includes a schematic front view of a monitoring device.

To collect this statistical information, a monitoring device 10 can be coupled to an exercise machine, such as a conventional treadmill 50, as shown in the figure (below). The figure shows a portion of a treadmill 50 from an end with a belt 52 mounted to revolve on a treadmill frame 54 (direction of belt movement indicated by arrow 20). The monitoring device 10 includes a mount 12 that is attachable to the treadmill frame 10 via any suitably secure device, such as glue, adhesive, tape, hook-and-loop fasteners, bolts, clips, interlocking parts, or screws. The mount 12 is positioned to attach to at least one side of the treadmill frame 54. In FIG. 1, the mount 12 is shown attached to both sides of the treadmill frame 54 above the belt 52 so that an axle 14 of the mount 12 extends across the belt 52. Alternatively, the mount 12 can be attached below or at an end of the treadmill 50. The mount 12 can be formed of any suitably rigid material, such as metal or plastic. The axle 14, also formed of any suitably rigid material such as metal or plastic, is fixed within the mount 12 and held at a distance (e.g., 1 cm to 10 cm) from the belt 52.

A rotational tracking device 16 is mounted to the axle 14 so that a portion of an outer edge is in contact the belt 52. Movement of the belt 52 in either direction rotates the rotational tracking device 16. The rotational tracking device 16 can be formed of any suitably firm material, such as rubber or plastic, but preferably includes non-skid material or material that engages readily with the belt 52 material to frictionally engage the belt 52. The rotational tracking device 16 includes a device, such as a gyroscope, accelerometer, or rotation counter, for measuring rotations of the rotational device during a given period with accuracy, and possibly a direction of rotation of the device. Alternatively, an optical tracker may track rotation of the rotational tracking device 16. For example, markers on the tracking device 16 may be employed (e.g. a camera or laser to track visible marker or markers on the tracking device 16) for use in tracking.

A vertical tracking device 18, such as an accelerometer, is also fixedly mounted on the axle 14. Vertical movement of the belt 52, e.g., as a result of impact with a user's feet, causes the rotational device 16 to push more or less on the axle, causing the axle to move vertically. The vertical tracking device 18 measures the resulting acceleration (up or down, relative to the belt 52) of this vertical movement with accuracy. As with the rotational tracking device 16, the vertical tracking device 18 may rely upon or employ optical trackers such as cameras or lasers in some implementations. Though shown as distinct, the vertical tracking device 18 and rotational tracking device 16 may be incorporated into the same physical tracker or other device.

The data, or statistical information, from the rotational tracking device 16 and the vertical tracking device 18 is communicated to a software application via a hardwire connection or wirelessly (e.g., via 802.11x wireless, Bluetooth, or ANT+). The software application may be stored on memory within the monitoring device 10 or on any suitable computing device, such as a mobile smart phone, a tablet computer, a laptop computer, or a desktop computer. The computing device can also include a display so that the data can be used to show information and analysis in real time.

When a user operates the treadmill for a run or walk, the user moves on the belt 52 as the belt is propelled by the treadmill 50. This propulsion is generally at a fixed rate, unless the user has selected to have the treadmill increase or decrease speed. However, as the user makes strides on the treadmill, the speed of the belt movement varies slightly due to impact of the user's feet with the belt. Specifically, there is slightly more frictional force when the runner's foot is down than when in the air, and the forward propulsive force applied by a user as he or she pushes off on the treadmill belt 52 slightly increases the speed of the belt 52. The rotational tracking device 16 can determine these relatively minor variations in the belt's speed. Further, the near-exact moment a foot touches down, and pushes off of the belt 52 may be detected by the vertical tracking device 16. Even relatively minor variations in the impact of the user's feet with the belt (i.e., downward force from the feet on the belt) can be determined by the vertical tracking device 18. The variations in this statistical information can be used to determine a physical activity analysis including aspects of the user's stride, such as push-off force and vertical landing force. These variations can also be used to determine treadmill cushion/dampening and also to suggest treadmill maintenance required due to inconsistency in treadmill speed.

In other examples, other data such as treadmill incline, cadence, stride length, contact time (e.g., the period where the user contacts the belt 52), flight time (e.g., the period where the user is not in contact with the belt 52), braking force (e.g., amount of braking the user causes while landing), symmetry between feet landing and push-off, and jump (e.g., vertical motion) can be determined based on the horizontal and vertical motion detected by the horizontal tracking device 16 and vertical tracking device 18. Determining a physical activity analysis can be used to provide the user with feedback, such as charts or other depictions like virtual representations. These can be shown visually on a display. The analysis may also be used as data fed into a virtual game environment where the data may drive an online avatar or propel a virtual character through a three-dimensional game world or images of the real world.

Braking occurs when a negative impulse to the treadmill belt 52 is detected, e.g., based on an encoder reading velocity in conjunction with an accelerometer registering user movement. Negative advancement or a negative advancement rate (i.e. a braking impulse) can be compared to a previously established primary (forward) direction of action of the treadmill belt that registers as a reduction in speed or a change of rotational direction of the encoder at a given threshold met by the accelerometer. This indicates a back drive of the treadmill belt based on the user landing or slowing down and thus a negative impulse to the belt.

In more detail, braking is a measure of speed lost due to negative force applied to the treadmill belt caused by the foot impacting the treadmill belt during gait. "Normal Speed" is determined during times during gait not including foot landing or foot push off from the belt. "Braking" is determined as the difference of speed from the "Normal Speed" and the "Landing Speed." "Landing Speed" is identified by the accelerometer from the slight change in speed of the belt as a result of the landing. "Push off Speed" is defined as the additional acceleration added to the treadmill belt during the force applied while accelerating the runner's body forward. "Push Off Speed" is determined when the accelerometer detects a push off based upon this acceleration. The "Push Off Acceleration" is the difference between a detected "Push Off Speed" and "Normal Speed."

Analyzing Braking and Pushoff can be used to benefit runner performance and health. Braking force has been shown to be strongly linked to injury and performance. Analyzing Pushoff can benefit performance by showing the effort produced for each step and incremental changes needed to improve running speed. If the Braking or Pushoff change throughout a run or from a statistical average (over many recorded runs), then there may be an injury, a potential injury, or a sign of fatigue or other issue where injury is more likely to take place. The system may track this data and inform the user of potential injury events or statistics that indicate such events may take place.

Bilateral symmetry of the legs can be evaluated based on accelerations in sagittal plane motion and a time contacting the belt by the user per each leg. Symmetry of user movement requires equal time spent with each foot contacting the ground and equal time in flight following push off from each of the legs following previous ground contact. This is measured by impulses registered by either or both of the vertical tracking device 18 and the rotational tracking device 16 for both push off and landing. Symmetry also includes equal landing impacts in both the vertical and horizontal directions, which can be detected by the vertical tracking device 18 in the relative vertical direction and the rotational tracking device 16 upon landing in the relative (based on incline) horizontal direction. Symmetry is also defined as equal push off impulses (e.g. the strength of each push off) detected by either or both of the rotational racking device 16 and the vertical tracking device 18. Vertical impact, ground contact time and flight time are also important in determining symmetry. If any aspect of symmetry is off, that may be tracked and noted.

A symmetry index (SI) is a difference in biomechanical measures between sides (left vs right side of the body). The SI includes an individual weighting of each metric, measured by the rotational tracking device 16 detecting horizontal motion of a treadmill belt (e.g., an encoder) and the vertical tracking device 18 detecting vertical motion of the treadmill deck (e.g., an accelerometer), to establish the differences in limb contribution for each step. For example:

$$SI = W_{gct} * GCT + W_{xpush} * XPush + W_{brk} * Brk + W_{valr} * VALR + W_{zpush} * ZPush + W_{flight} * Flight$$

where each metric is the right side to left side difference in each measure:

W=weighting constant for each metric
GCT=ground contact time of each step
XPush=Force of pushoff in the horizontal direction to propel the runner forward
Brk=The negative force applied upon the treadmill belt during landing
VALR=Vertical average loading rate
ZPush=Vertical push off force
Flight=time in the air between foot contact.

Said another way, these measurements are a weighted constant to generate a reliable index over typical data, a measure of the time each foot is touching the rotating belt, a measure of a pushoff force of the runner in a direction coincident with rotation of the rotating belt, a measure of a braking force applied in a direction contrary to rotation of the rotating belt by a runner on footfall, a measure of a vertical force applied upon footfall by the runner on the rotating belt, a measure of a vertical force applied upon push off by the runner on the rotating belt, and the time between pushoff and footfall for each step by a runner on the rotating belt.

The Symmetry Index can be used to determine the progression of fitness demonstrated by improvement or stabilization of bilateral symmetry, meaning that as a runner's technique improves, the Symmetry Index should likewise improve such that a runner's gait becomes more symmetrical. In addition, depending on the type of running a runner wishes to excel at, push off force may be more important than flight time or vice versa. With detailed statistics provided by the Symmetry Index, training regimen may focus on desired stride characteristics more specifically and track associated changes in the Symmetry Index as a result of training.

The Symmetry Index demonstrates fatigue by displaying side-by-side differences from the normative symmetry values established during non-fatigued activity. The user may be warned with the data itself, or a derivative of the data (e.g. a warning). The data may be stored over long periods of time to note improvements or detriments and times during when fatigue, longer runs, or other states of suboptimal and optimal running symmetry were found.

Users, and their doctors and trainers, can use this physical activity analysis described above to make adjustments to their exercise and training routines, medical procedures, physical therapy, nutrition, and any other aspects of their health and wellness routines, to better improve these aspects. For example, certain physical activity analysis determines can be correlated with these aspects, and provide an indicator of adjustments that need to be made. In one example, the physical activity analysis may indicate an asymmetry due to uneven leg length where shoe insert orthotics can be beneficial. In another example, the physical activity analysis may indicate a prolonged braking caused by poor form where the user is not properly lifting their toes during each stride. This information could be used to determine that the user should perform certain exercises to improve their ability to lift their toes during each stride.

Figure 2:
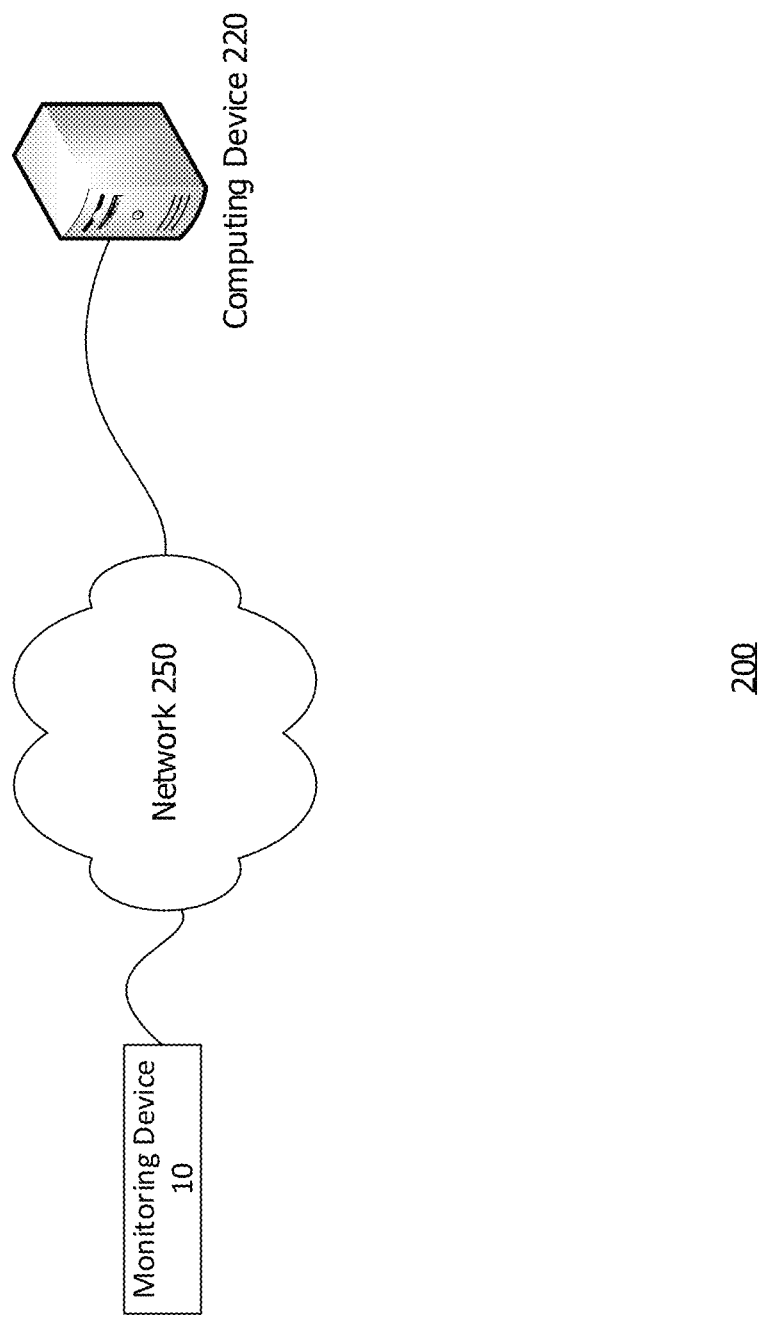
FIG. 2 is an overview of a system for monitoring physical movement.

Referring now to FIG. 2, an overview of a system 200 for monitoring physical movement is shown. The system 200 includes the monitoring device of FIG. 1 and a computing device 220, interconnected by a network 250.

The monitoring device 10 may include a computer for performing analysis of the data from the rotational tracking device and the vertical tracking device, and generating analysis and images displayed on a display, or those capabilities may be offloaded to a remote computing device, such as computing device 220 or otherwise to cloud computing capabilities.

The computing device 220 is a computing device (FIG. 4) that is connected to the monitoring device 10 via the network. The computing device 220 may offer its computational capabilities to the monitoring device for, for example, storing data obtained by the monitoring device, calculating user statistics based on the data, and displaying the data and the statistics.

The network 250 is a system for passing data between the monitoring device 10 and the computing device 220. The network may be or include the Internet, as well as various systems such as Bluetooth®, ANT+, Ethernet, 802.11x wireless networking, short-range RF frequency wireless networking systems, and other network types capable of passing data between the other components of the system 200. Alternatively, the monitoring device 10 may be directly coupled to the computing device 220 via a physical connection (i.e., hard-wired connection).

Figure 3:
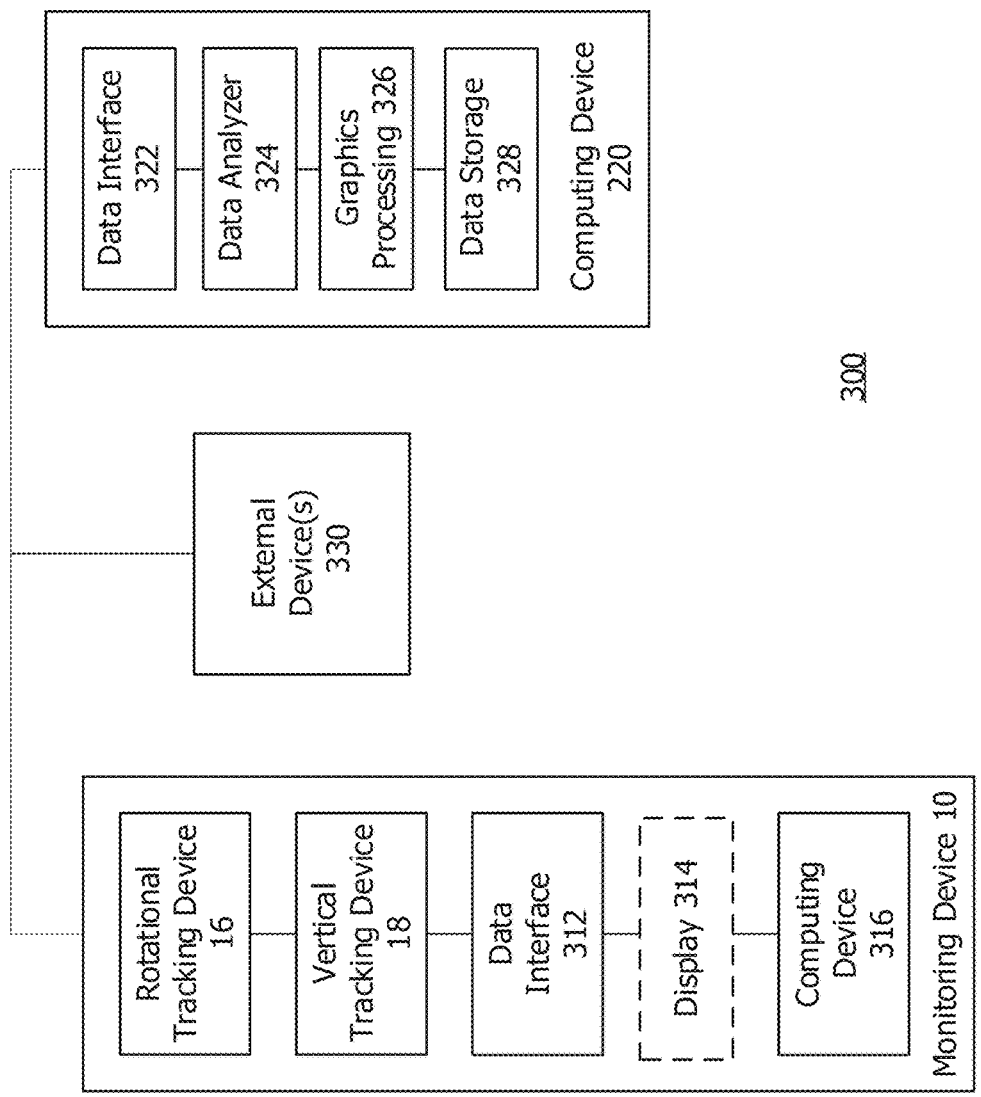
FIG. 3 is a functional block diagram of a system for monitoring physical movement.

FIG. 3 is a functional block diagram of a system 300 for monitoring physical activity. The system 300 includes the monitoring device 10 of FIG. 1 and computing device 220 of FIG. 2, as well as optional external device(s) 330.

The monitoring device 10 includes rotational tracking device 16 and vertical tracking device 18, as described previously, and may include a data interface 312, a display 312, and a computing device 316. These components are described functionally, because it aids in understanding of the overall system, but they may be implemented in one or more physical systems or components.

The data interface 312 is used to exchange data between the monitoring device 10, the computing device 220, and the external device(s) 330. The data interface 312 may be or include the Internet or Internet access and may rely upon various physical and logical systems or protocols such as those described above.

The display 314 is an optional system for displaying a status, data, or data analysis including graphs, charts, and indicators, from the monitoring device 10, and can be any suitable type of display such as an LCD or LED screen.

The computing device 316 may be a general-purpose computing device (e.g. FIG. 4) or may be a specialized computing device. The computing device 316 may perform the entire process of analyzing data from the monitoring device 10 and any external devices(s) 330, and displaying the data and analysis on the display 314. The computing device 316 may, instead, offload much of that to external capabilities, and only be responsible for directing the capture of data that is provided to the computing device 220, and transmitting data, using the data interface 312, generated by the rotational tracking device 16 and the vertical tracking device 18.

The external device(s) 330 may provide additional data. The external device(s) 330 are external in the sense that they are separate from the monitoring device 10 and the computing device 220, but they may take many forms. The external device(s) 330 may provide data from a treadmill, such as incline of the treadmill, speed of rotation of the belt of the treadmill, power exerted, dimensions and specifications of the treadmill, and physical characteristics of the user such as height, weight, gender, age, and/or heart rate. The external device(s) 330 may also be or include a sensor or health tracking device, such as a wearable device like a watch, fitness band, or chest strap, that provides data for additional analysis, such as heart rate, blood pressure, sleep information, etc.

The computing device 220 includes a data interface 322, data analyzer 324, graphics processing 326, and data storage 328. These components are described functionally, because it aids in understanding of the overall system, but they may be implemented in one or more physical systems or components. The computing device 220 may be a server, physically near or remote from the monitoring device 10. The computing device 220 may be integrated into the monitoring device 10, but may be distinct from it, and connected by a high-speed data transmission including wired or wireless communications. The computing device 220 may be an external personal computing device such as an iPad®, personal computer, Apple TV®, or other, similar device.

The data interface 322 is used to exchange data between the monitoring device 10 and the computing device 220 and the external device(s) 330. The data interface 322 may be or include the Internet or Internet access and may rely upon various physical and logical systems or protocols such as those described above.

The data analyzer 324 is or includes a processor for analyzing data received from the monitoring device 10 and/or the external device(s) 330, e.g., such as performing calculations to determine aspects of a user's performance and determine a physical activity analysis.

The graphics processing 326 is or includes a processor for generating graphical representation of the data, the user's performance, and/or a physical activity analysis on a display. The graphics processing 326 may be or include a GPU (graphics processing unit). The graphics processing 326 is used to generate the graphics, e.g., real-time or historical, that are representative of the data, the user's performance, and/or a physical activity analysis for display on the display. The graphics processing 326 may also generate a game or virtual environment through which a runner on a treadmill moves and display that game or environment on a display.

The data storage 328 is storage for user information, data, physical activity analysis, and graphics created using the computing device 220. The data storage 328 may also act as a long-term repository for data that may be accessed by the user in the future.

Figure 4:
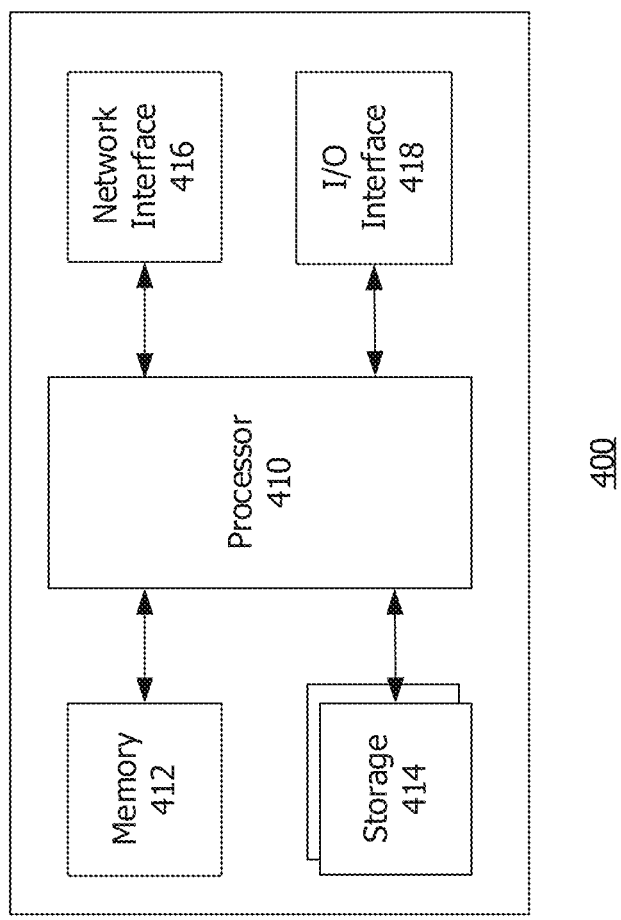
FIG. 4 is a computing device.

Turning now to FIG. 4, a block diagram of a computing device 400 is shown. The computing device 400 may be representative of the server computers, client devices, mobile devices and other computing devices discussed herein. The computing device 400 may include software and/or hardware for providing functionality and features described herein. The computing device 400 may therefore include one or more of: logic arrays, memories, analog circuits, digital circuits, software, firmware and processors. The hardware and firmware components of the computing device 400 may include various specialized units, circuits, software and interfaces for providing the functionality and features described herein.

The computing device 400 may have a processor 410 coupled to a memory 412, storage 414, a network interface 416 and an I/O interface 418. The processor 410 may be or include one or more microprocessors and application specific integrated circuits (ASICs).

The memory 412 may be or include RAM, ROM, DRAM, SRAM and MRAM, and may include firmware, such as static data or fixed instructions, BIOS, system functions, configuration data, and other routines used during the operation of the computing device 400 and processor 410. The memory 412 also provides a storage area for data and instructions associated with applications and data handled by the processor 410. As used herein, the word memory specifically excludes transitory medium such as signals and propagating waveforms.

The storage 414 may provide non-volatile, bulk or long-term storage of data or instructions in the computing device 400. The storage 414 may take the form of a disk, tape, CD, DVD, SSD, or other reasonably high capacity addressable or serial storage medium. Multiple storage devices may be provided or available to the computing device 400. Some of these storage devices may be external to the computing device 400, such as network storage or cloud-based storage. As used herein, the word storage specifically excludes transitory medium such as signals and propagating waveforms.

The network interface 416 is responsible for communications with external devices using wired and wireless connections reliant upon protocols such as 802.11x, Bluetooth®, Ethernet, satellite communications, and other protocols. The network interface 416 may be or include the internet.

The I/O interface 418 may be or include one or more busses or interfaces for communicating with computer peripherals such as mice, keyboards, cameras, displays, microphones, and the like.

Description of Processes

Figure 5:
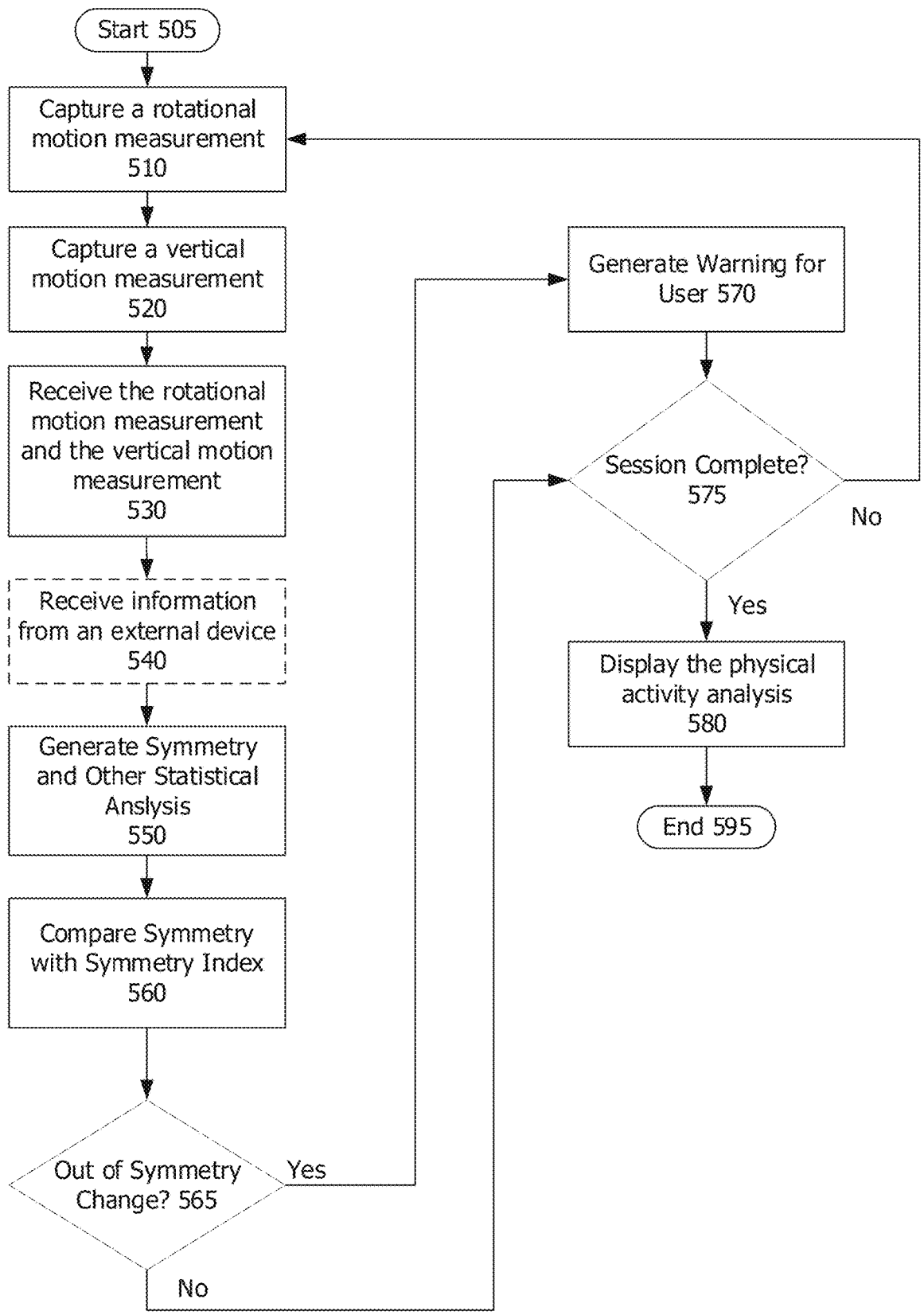
FIG. 5 is a flowchart of a process for monitoring physical movement.

FIG. 5 is a flowchart of a process for monitoring physical activity. The flowchart has a start 505 and an end 595, but the overall process may take place many times over in rapid succession or simultaneously.

Following the start 505, the process begins with capture of a rotational motion measurement 510. For example, as discussed with respect to FIG. 1, the rotational tracking device 16 generates a rotational movement of the belt 52, which may be a speed of the belt. This data can be received by a computing device, where it can then be stored and analyzed. By generating multiple of measurements during even a short period of time (e.g. multiple measurements per second), the data from the rotational motion device can be used to determine whether the belt is accelerating or decelerating rotationally (e.g., horizontally), and any speed or acceleration changes in the belt over that period.

The process continues with capturing a vertical motion measurement at 520. For example, as discussed with respect to FIG. 1, the vertical tracking device 18 determines a vertical motion of the belt 52, which may be a vertical acceleration or deceleration of the belt. This data can be received by a computing device, where it can then be stored and analyzed. By considering a number of measurements during a period, the data from the vertical motion device can be used to determine whether the belt is accelerating or decelerating vertically over that period.

At step 530, the rotational motion measurement and the vertical motion measurement are received by a computing device. As described above, the computing device can be a separate computing device or can be integrated into the monitoring device. The computing device can then store the measurements for calculations and analysis.

At step 540, the computing device optionally receives information from an external device, such as the treadmill or wearable device, as described above. This information can include information about the treadmill, such as an incline, dimensions of the rotational belt, power output of the treadmill, or any other information that could be relevant to determining physical activity analysis. The information can also include further information about the user, such as age, gender, height, weight, fitness level, heart rate, blood pressure, health issues such as diabetes or stroke, and any other information that could be relevant to determining physical activity analysis.

At step 550, the computing device can generate a Symmetry Index, as discussed above, along with a physical activity analysis based on the rotational motion measurement, the vertical motion measurement, and optionally information from the external device. The Symmetry Index may take into account each of the variables described above, based upon data gathered in a most recent series of data capture steps (e.g. steps 510 and 520) and update its data for both the long-term Symmetry Index and the immediate one (e.g. the one over the last minute, several minutes, or this workout session). In fact, multiple Symmetry Indexes may be created for various time frames as an individual is exercising. In this way, changes may be detected relative to all time, but also for a given exercise session.

The computing device can use all of the information, a portion of the information from a certain period in the calculation, or only certain information to determine a physical activity analysis. The computing device can determine multiple different physical activity analyses based on different types of information and information from different periods. For example, the computing device could determine an asymmetry physical activity analysis based on information from the rotational tracking device, the vertical tracking device, and an external device (e.g., incline information from the treadmill). In another example, the computing device can determine a form physical activity analysis based on information from the rotational tracking device, the vertical tracking device, and user information such as height and gender. In another example, the computing device could determine an injury physical activity analysis based on information from the rotational tracking device, the vertical tracking device, an external device, and user input.

At 560, the symmetry of a given time frame (e.g. the last minute of exercise) may be compared with a number of Symmetry Indexes for a given exercising individual. If there is a significant variance, a variance over a predetermined threshold, then a warning may be generated for the user at 570. These thresholds may vary based upon the time frame of the comparison. For example, if a given exerciser has a variance of between 0.04 of a second from landing to pushoff over the course of his or her exercise life, then a symmetry index calculated for the last thirty seconds that indicates that that user has one leg that has 0.05 second difference in landing/pushoff symmetry may not reach a threshold of relevant difference from the typical Symmetry Index. However, a variance of 0.1 second may rise to a sufficient level to breach a threshold sufficient to generate a warning for the user at 570. Various thresholds may be used for each different component of the Symmetry Index or for the Symmetry Index as a whole over a given time frame.

These thresholds may be set for the Symmetry Index as a whole, or may be for individual characteristics measured, as discussed above. Preferably, it is a comparison of the Symmetry Index as a whole over a short timeframe (e.g. 1 minute) compared with a typical lifetime average or average over the course of an entire run (e.g. 30 minutes or several hours, depending on the runner's typical exercise regimen). Symmetry may naturally degrade as an exerciser becomes tired, but this also may indicate the possibility of an injury. Still, the Symmetry Index compared may be taken from a typical exercise routine at around the same time so as to compare the symmetry of a runner's gait at the same time in the present routine.

This determination whether a given timeframe is too far out of symmetry is made at 565 with a view to warning the exerciser that their stride has varied from an ideal symmetry, and as a result, the exerciser may be injured, or may experience injury soon. If the symmetry of the recent timeframe is too large ("yes" at 565), then that warning is generated at 570. If it is not ("no" at 565), then the process continues to 575.

At 575, a determination is made whether the exercise session is complete. If not ("no" at 575), then the process continues with more capture of rotational and vertical movement at 510. If so ("yes" at 575), then the process proceeds to 580.

At step 580, the computing device can display information that is useful to the user, such as one or more physical activity analysis, user input information, information from an external device, measurements from the rotational tracking device and the vertical tracking device, and correlations between one or more of these information types. For example, different types of information may be best displayed as a chart, a graph, a moving graphic, a table, a diagram, or another display format. The user may be able to choose between different types of display formats, and which information is displayed.

Optionally, the user may be able to store or download the information and the analysis so that it can be compared with other information obtained at a different time. The user may also share the information with a trainer, a doctor, or other health and fitness professional so that the professional can help the user interpret the data and determine a plan of action in response to the data. For example, the professional may instruct the user in better form, nutrition, separate exercises, or physical aides such as braces, shoes, or orthotics.

Then the process may end at 595. However, the entire process may be continually repeated, and/or individual steps of the process may be continually repeated. For example, the rotational measurement and the vertical motion measurement may be continuously made while the user is using the treadmill. The measurements may be continually sent to the computing device, and the computing device may continually determine and display a physical activity analysis. Once the user has finished the physical activity, different physical activity analysis can be performed on the measurements. For example, physical activity analysis can be performed on only certain periods of the physical activity or only using certain measurements or information from an external device. The user may also modify how the analysis, measurements, and information is displayed, such as in charts, graphs, spreadsheets, or other graphics.

CLOSING COMMENTS

Throughout this description, the embodiments and examples shown should be considered as exemplars, rather than limitations on the apparatus and procedures disclosed or claimed. Although many of the examples presented herein involve specific combinations of method acts or system elements, it should be understood that those acts and those elements may be combined in other ways to accomplish the same objectives. With regard to flowcharts, additional and fewer steps may be taken, steps may be taken in a different order, and the steps as shown may be combined or further refined to achieve the methods described herein. Acts, elements and features discussed only in connection with one embodiment are not intended to be excluded from a similar role in other embodiments.

As used herein, "plurality" means two or more. As used herein, a "set" of items may include one or more of such items. As used herein, whether in the written description or the claims, the terms "comprising", "including", "carrying", "having", "containing", "involving", and the like are to be understood to be open-ended, i.e., to mean including but not limited to. Only the transitional phrases "consisting of" and "consisting essentially of", respectively, are closed or semi-closed transitional phrases with respect to claims. Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. As used herein, "and/or" means that the listed items are alternatives, but the alternatives also include any combination of the listed items.

It is claimed:

1. A method for monitoring movement comprising:
   determining a rotational motion measurement of a rotating belt of a treadmill via a rotational tracking device, wherein a movement monitoring device comprising the rotational tracking device is configured to engage with the rotating belt while the treadmill is in use by a user, and wherein the rotational tracking device is configured to send the rotational motion measurement to a computing device; and
   determining a vertical motion measurement of the belt via a vertical tracking device, wherein the movement monitoring device further comprises the vertical tracking device, and wherein the vertical tracking is configured to send the vertical motion measurement to the computing device;
   receiving, by the computing device, the rotational motion measurement and the vertical motion measurement; and
   generating, by the computing device, a Symmetry Index for the user on the rotating belt of the treadmill, the Symmetry Index being a comparison of more than one measure of symmetry for a first leg and a second leg of the user derived from the rotational motion measurement and the vertical motion measurement, wherein the computing device generates a warning to the user if the Symmetry Index falls outside of a threshold that suggests that injury may be possible.

2. The method of claim 1, wherein the more than one measure of symmetry is chosen from the group comprising:
   a measure of the time each foot of the user is touching the rotating belt;
   a measure of a pushoff force of the user in a direction coincident with rotation of the rotating belt;
   a measure of a braking force applied in a direction contrary to rotation of the rotating belt by the user on footfall;
   a measure of a vertical force applied upon footfall by the user on the rotating belt;
   a measure of a vertical force applied upon push off by the user on the rotating belt; and
   a time between pushoff and footfall for each step by the user on the rotating belt.

3. The method of claim 2, wherein the computing device generates the Symmetry Index using all of the at least one measures of symmetry.

4. The method of claim 2, wherein the rotational motion measurement is used to generate:
   the measure of a pushoff force of the user in a direction coincident with rotation of the rotating belt;
   the measure of a braking force applied in a direction contrary to rotation of the rotating belt by the user on footfall; and
   the time between pushoff and footfall for each step by the user on the rotating belt.

5. The method of claim 2, wherein the vertical motion measurement is used to generate:
   the measure of a vertical force applied upon footfall by the user on the rotating belt;
   the measure of a vertical force applied upon push off by the user on the rotating belt; and
   the time between pushoff and footfall for each step by the user on the rotating belt.

6. The method of claim 1, wherein the rotational motion measurement comprises at least one of a rotational speed of the belt and a change in rotational speed of the belt.

7. The method of claim 1, wherein the vertical motion measurement comprises a magnitude of a vertical acceleration of the belt.

8. The method of claim 1, wherein the rotational tracking device or the vertical tracking device includes one of the following an accelerometer, a gyroscope, a gravitometer, a video camera, an infrared camera, or a laser.

9. The method of claim 1, wherein the computing device is further for generating speed, distance, and time measurements for the user using the rotational motion measurements and the vertical motion measurements throughout an exercise routine.

10. The method of claim 1, wherein the computing device generates a warning to the user if the Symmetry Index of a given time frame for differences in a plurality of times between pushoff and footfall for each step by the user on the rotating belt for the first leg as compared to the second leg falls outside of a threshold that suggests that injury may be possible.

11. The method of claim 1, wherein the computing device generates a warning to the user if the Symmetry Index, over a short time frame compared with an average over the total course of a run, for differences in a plurality of times between pushoff and footfall for each step by the user on the rotating belt for the first leg as compared to the second leg falls outside of a threshold that suggests that injury may be possible.

12. A method for monitoring movement comprising:
    determining a rotational motion measurement of a rotating belt of a treadmill via a rotational tracking device, wherein a movement monitoring device comprising the rotational tracking device is configured to engage with the rotating belt while the treadmill is in use by a user, and wherein the rotational tracking device is configured to send the rotational motion measurement to a computing device; and
    determining a vertical motion measurement of the belt via a vertical tracking device, wherein the movement monitoring device further comprises the vertical tracking device, and wherein the vertical tracking is configured to send the vertical motion measurement to the computing device;
    generating, by the computing device, a Symmetry Index for the user on the rotating belt of the treadmill, the Symmetry Index being a comparison of more than one measure of symmetry for a first leg and a second leg of the user derived from the rotational motion measurement and the vertical motion measurement, wherein the computing device generates a warning to the user if the Symmetry Index falls outside of a threshold that suggests that injury may be possible.

13. The method of claim 12, wherein the more than one measure of symmetry is chosen from the group comprising:
- a measure of the time each foot of the user is touching the rotating belt;
- a measure of a pushoff force of the user in a direction coincident with rotation of the rotating belt;
- a measure of a braking force applied in a direction contrary to rotation of the rotating belt by the user on footfall;
- a measure of a vertical force applied upon footfall by the user on the rotating belt;
- a measure of a vertical force applied upon push off by the user on the rotating belt; and
- a time between pushoff and footfall for each step by the user on the rotating belt.

14. The method of claim 13, wherein the computing device generates the Symmetry Index using all of the at least one measures of symmetry.

15. The method of claim 13, wherein the rotational motion measurement is used to generate:
- the measure of a pushoff force of the user in a direction coincident with rotation of the rotating belt;
- the measure of a braking force applied in a direction contrary to rotation of the rotating belt by the user on footfall; and
- the time between pushoff and footfall for each step by the user on the rotating belt.

16. The method of claim 13, wherein the vertical motion measurement is used to generate:
- the measure of a vertical force applied upon footfall by the user on the rotating belt;
- the measure of a vertical force applied upon push off by the user on the rotating belt; and
- the time between pushoff and footfall for each step by the user on the rotating belt.

17. The method of claim 12, wherein the rotational motion measurement comprises at least one of a rotational speed of the belt and a change in rotational speed of the belt.

18. The method of claim 12, wherein the vertical motion measurement comprises a magnitude of a vertical acceleration of the belt.

19. The method of claim 12, wherein the rotational tracking device or the vertical tracking device includes one of the following an accelerometer, a gyroscope, a gravitometer, a video camera, an infrared camera, or a laser.

20. The method of claim 12, wherein the computing device is further for generating speed, distance, and time measurements for the user using the rotational motion measurements and the vertical motion measurements throughout an exercise routine.

21. The method of claim 12, wherein the computing device generates a warning to the user if the Symmetry Index of a given time frame for differences in a plurality of times between pushoff and footfall for each step by the user on the rotating belt for the first leg as compared to the second leg falls outside of a threshold that suggests that injury may be possible.

22. The method of claim 12, wherein the computing device generates a warning to the user if the Symmetry Index, over a short time frame compared with an average over the total course of a run, for differences in a plurality of times between pushoff and footfall for each step by the user on the rotating belt for the first leg as compared to the second leg falls outside of a threshold that suggests that injury may be possible.

* * * * *